(12) United States Patent
Orehek

(10) Patent No.: US 8,708,906 B1
(45) Date of Patent: Apr. 29, 2014

(54) METHOD FOR THE PREVENTION OF DEMENTIA AND ALZHEIMER'S DISEASE

(76) Inventor: Allen J. Orehek, Waymart, PA (US)

( * ) Notice: Subject to any disclaimer, the term of this patent is extended or adjusted under 35 U.S.C. 154(b) by 254 days.

(21) Appl. No.: 13/227,137

(22) Filed: Sep. 7, 2011

(51) Int. Cl.
*A61B 5/00* (2006.01)
*G06F 19/00* (2011.01)

(52) U.S. Cl.
CPC ........... *G06F 19/3431* (2013.01); *A61B 5/7292* (2013.01); *A61B 5/4088* (2013.01)
USPC ......................................... 600/301

(58) Field of Classification Search
USPC .......................................... 600/300, 301, 544
See application file for complete search history.

(56) References Cited

U.S. PATENT DOCUMENTS

| | | | | |
|---|---|---|---|---|
| 5,994,080 | A * | 11/1999 | Grobbee et al. | 435/6.11 |
| 6,040,147 | A * | 3/2000 | Ridker et al. | 435/7.24 |
| 6,112,750 | A * | 9/2000 | Chandra | 128/898 |
| 8,346,573 | B2 * | 1/2013 | Glimp et al. | 705/2 |
| 2006/0025658 | A1 * | 2/2006 | Newman et al. | 600/301 |
| 2007/0196520 | A1 * | 8/2007 | Lin et al. | 424/739 |
| 2007/0280917 | A1 * | 12/2007 | Helgadottir et al. | 424/94.1 |
| 2007/0299360 | A1 * | 12/2007 | Snyder et al. | 600/544 |
| 2008/0088629 | A1 * | 4/2008 | Lorenz et al. | 345/440.2 |
| 2008/0228043 | A1 * | 9/2008 | Kenedy et al. | 600/300 |
| 2008/0279846 | A1 * | 11/2008 | Shi et al. | 424/130.1 |
| 2009/0024003 | A1 * | 1/2009 | Schoemaker | 600/300 |
| 2010/0021533 | A1 * | 1/2010 | Mazed et al. | 424/450 |
| 2011/0052736 | A1 * | 3/2011 | Romero et al. | 424/739 |
| 2012/0034193 | A1 * | 2/2012 | Rees et al. | 424/93.7 |

* cited by examiner

*Primary Examiner* — Bill Thomson
*Assistant Examiner* — Bobby Soriano
(74) *Attorney, Agent, or Firm* — Caesar, Rivise, Bernstein, Cohen & Pokotilow, Ltd.

(57) ABSTRACT

A method for the prevention of dementia is provided including the steps of testing, in a client, for a dementia risk factors (including those related to brain tissue, atrial fibrillation, hypercoaguable state, LDL cholesterol, carotid artery evaluation, tobacco use, hypertension, and inflammation evaluation), determining a score for each of the risk factors tested, wherein each score is based on a continuous scale from a low number to a high number, wherein a low number corresponds to a relatively low likelihood of dementia risk and a high number corresponds to a relatively low likelihood of dementia risk, applying all of the scores obtained to an equation that yields a resulting value proportional to an overall risk of dementia, and providing dementia risk reduction advice to the client to lower the scores for each of the components.

4 Claims, 12 Drawing Sheets

US 8,708,906 B1

METHOD FOR THE PREVENTION OF DEMENTIA AND ALZHEIMER'S DISEASE

BACKGROUND OF THE INVENTION

The present invention is directed to a mode of treatment of a client to prevent dementia and Alzheimer's disease.

For purposes of the present invention, dementia is defined to include Alzheimer's disease. Unmodified dementia risk is the population of the world. Millions of people in the world are affected with dementia. Cost of the disease is in the billions to trillions. As of 2010, there are approximately 5.3 million in the United States having dementia, requiring approximately 172 billion dollars to treat. It is the sixth leading cause of death. There are 10.9 million unpaid caregivers and an untold cost in pain and suffering.

All references cited herein are incorporated herein by reference in their entireties.

BRIEF SUMMARY OF THE INVENTION

A method for the prevention of dementia is provided including the steps of testing, in a client, for a dementia risk factors (including those related to brain tissue, atrial fibrillation, hypercoaguable state, LDL cholesterol, carotid artery evaluation, tobacco use, hypertension, and inflammation evaluation), determining a score for each of the risk factors tested, wherein each score is based on a continuous scale from a low number to a high number, wherein a low number corresponds to a relatively low likelihood of dementia risk and a high number corresponds to a relatively high likelihood of dementia risk, applying all of the scores obtained to an equation that yields a resulting value proportional to an overall risk of dementia, and providing dementia risk reduction advice to the client to lower the scores for each of the components.

The method for prevention of dementia may include testing all of the components, including brain tissue, atrial fibrillation, hypercoaguable state, LDL cholesterol, carotid artery evaluation, tobacco use, hypertension, and inflammation evaluation. The method is preferably performed by center specializing in medical prevention and the testing is certified for quality of consistency by the center.

The equation that yields a resulting value proportional to an overall risk of dementia may be:

$$n = \frac{500}{4\pi a^2} + \frac{1000}{4\pi b^2} + \frac{1000}{4\pi g^2} + \frac{1100}{4\pi c^2} + \frac{600}{4\pi h^2} + \frac{900}{4\pi t^2} + \frac{800}{4\pi y^2} + \frac{900}{4\pi d^2} + \frac{400}{4\pi i^2} + \frac{1100}{4\pi x^2}$$

where:

n=a value used in risk of dementia score/final score expressed as a percent of chance to develop dementia in this client;

a=a value calculated from atrial fibrillation component;
b=a value calculated from brain tissue component;
g=a value calculated from LDL component;
c=a value calculated from carotids component;
h=a value calculated from hypercoaguable state component;
t=a value calculated from tobacco component;
y=a value calculated from hypertension component;
d=a value calculated from diabetes component;
i=a value calculated from systemic inflammation component; and
x=a value calculated from secondary components.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1:
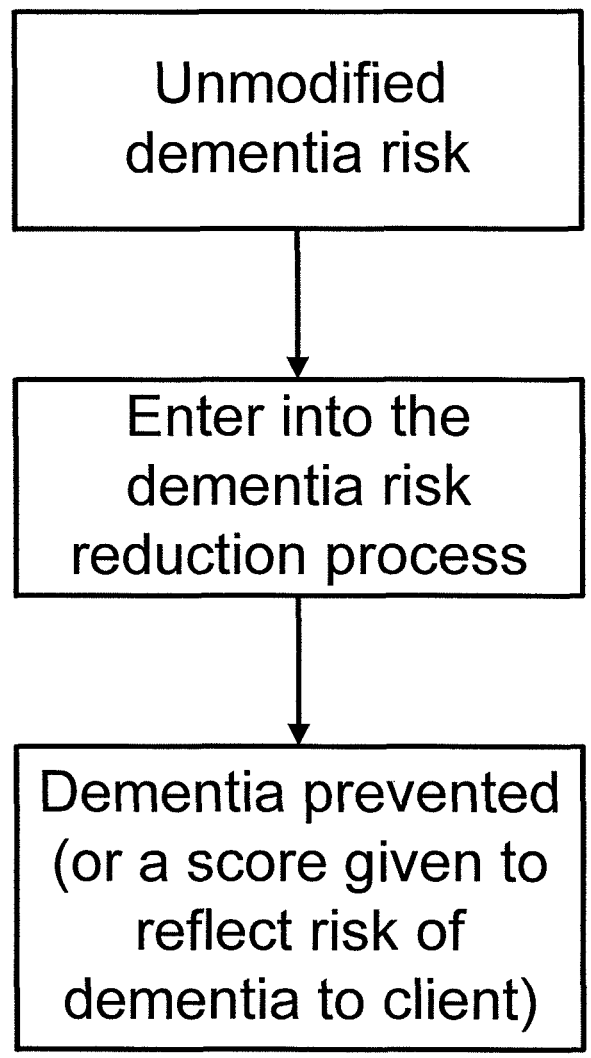
FIG. 1 is flowchart of an overall method for the prevention of dementia in accordance with a preferred embodiment of the present invention.

The present invention is directed to a method for preventing dementia, including Alzheimer's disease. The method involves obtaining data, by performing studies from a client (e.g., performing tests, obtaining history from client, asking the client questions, etc.) with respect to numerous components that can impact a client's risk for developing dementia.

The invention will be illustrated in more detail with reference to the following embodiments, but it should be understood that the present invention is not deemed to be limited thereto.

Overall Medical Prevention:

While the present invention is directed specifically to a method for preventing dementia, it is part of an overall method for preventing or decreasing the likelihood of various cancers and dementia. In the overall method, a prefix "1" through "16" is used to designate sixteen types of health related issues for an overall method of decreasing cancer and dementia related problems. The method of preventing dementia of the present invention is designated as category "2." The sixteen health related issues are shown in Table 1 below, which indicates 1 through 16 categories.

TABLE 1

| | |
|---|---|
| 1 | Colorectal Cancer |
| 2 | Dementia |
| 3 | Thyroid Cancer |
| 4 | Breast Cancer |
| 5 | Testicular Cancer |
| 6 | Pancreas Cancer |

TABLE 1-continued

| | |
|---|---|
| 7 | Liver Cancer |
| 8 | Kidney Cancer |
| 9 | Ovarian Cancer |
| 10 | Abdominal Aortic Aneurysm |
| 11 | Ascending Aortic Aneurysm |
| 12 | Coronary Artery Disease |
| 13 | Stomach/Esophageal Cancer |
| 14 | Malignant Melanoma |
| 15 | Cervical Cancer |
| 16 | Uterine Cancer |

In the overall process, a total score is obtain by separately scoring each of the above sixteen categories and using these separate scores in an equation to arrive at an overall score. There may be at least two levels of testing with associated scoring performed for each of the above sixteen categories. For each of the sixteen categories above, a numerical score is applied from 1 to 85, where 1 is a failure (there is no way to benefit here from any reduction) and 85 is the best passing score possible. The score for a particular client for a particular category includes a prefix of 1, 2, 3, etc., which is associated with one of the above categories. For example, for dementia (category 2), a particular client's overall score may range from 2.1 to 2.85. Scores between 2.1 and 2.85 are assigned based upon specific criteria, as will be described below. However, it must be noted that the criteria that affect the various scores between 1 and 85 are somewhat "liquid" in that they may change over time with new advances in technology or current scientific data. Since anything involving medical technology is not 100% accurate or predictable, the highest scores for this method indicate, generally, an 85 percent confidence.

The overall process is an effort to reduce the risk of development of the above cancers from spreading or the above disease processes from developing. In the overall process, risk associated with each of the above quantified in a manner similar to that for dementia as described herein. For each of the 16 categories, a separate score will be assigned, as described above. A final 'grand total' score is determined, once all 16 areas have been properly evaluated. For present purposes, the scores will be determined by a medical prevention center (MPC) by using results of various medical tests and the like.

It is noted that there are about 200 types of cancer involving about 60 organs. The overall method can, of course, be expanded to include more of these types of cancer.

Assigning a final overall score in this manner offers numerous benefits. For example, where a potential new CEO of a company is critical to the success of the company, a sufficiently high score from a medical prevention center will allow the company's board or owners to have some assurance that there will not be any sudden stock fall due to death or illness of the CEO. Additionally, for example, for a potential three year professional football contract, a team may require that a certain overall score be determined by a medical prevention center to "certify" that player to give some assurance that the player will not die from, for example, a rupturing ascending aortic aneurysm. An additional example of the usefulness of the present method is for life insurance and/or health insurance. A client who gains a high overall score could be entitled to a significant reduction in any fees.

The method of the present invention has an analogy in a rope: A person is holding on to a rope and is sliding down the rope through his or her life. When the bottom of the rope is reached, dementia occurs. The rope can break and the person gets dementia. Once the person slides to the bottom of the rope, he or she gets dementia. The rope has two aspects, length and thickness. The longer the rope the better as it gives some ability to slip here and there before reaching the end of the rope. The thicker the rope the better as the person has a stronger rope to hold onto. The length of the rope is decided by the primary pathway. The thickness of the rope is decided by the secondary pathway issues, as will be described.

Method of Prevention of Dementia

Figure 2:
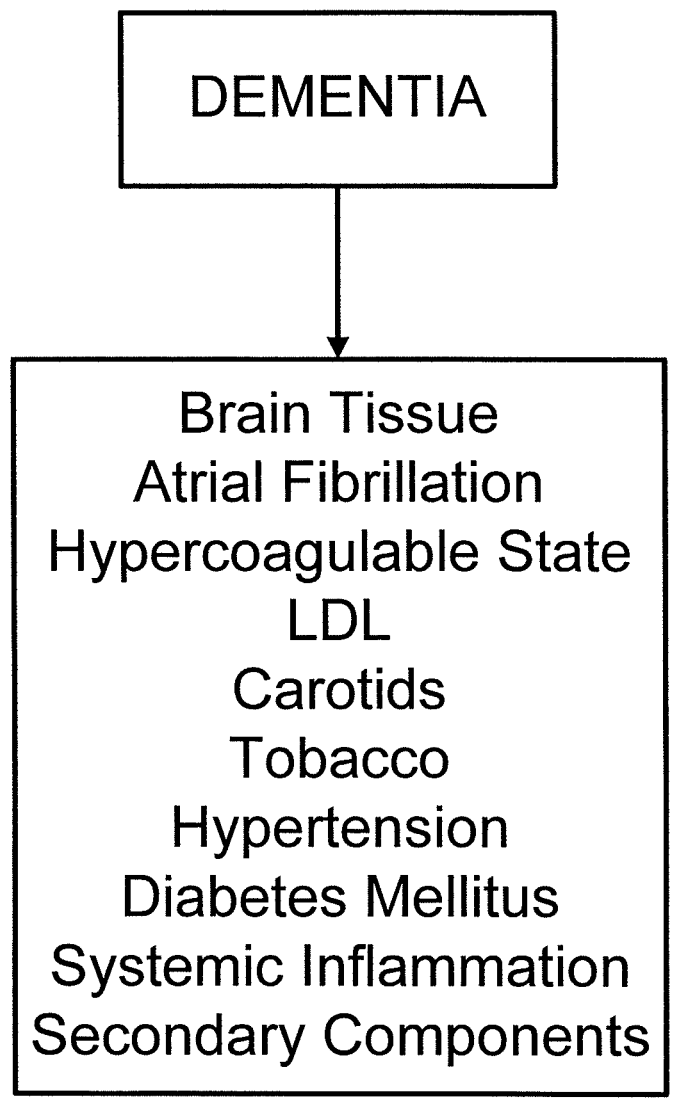
FIG. 2 is flowchart of the components analyzed in the method of preventing dementia in of FIG. 1, showing ten components analyzed in the method.

The present invention is specifically directed to the dementia pathway, i.e., the steps taken to reduce dementia (designated as "2" as discussed above). As shown in FIG. 1, a client begins with an "unmodified dementia risk" which is the overall risk of developing dementia for all people in the world. The client is put through a specific dementia risk reduction analysis which includes obtaining data with respect to nine dementia risk factors, including, brain tissue, atrial fibrillation, hypercoaguable state, LDL cholesterol, carotid artery evaluation, tobacco use, hypertension (HTN), diabetes mellitus, and systemic inflammation. See FIG. 2. Of course, more or fewer dementia risk factors can be analyzed. The nine of ten dementia risk factors here is merely an example. The method of the present invention continues with the step of determining what lifestyle and other changes must be made so that the client either does not develop dementia or has or her risk for developing dementia reduced.

The prefix "i" is used to designate the overall score for dementia which is calculated from scores achieved in the nine components in the dementia category. The prefix "ii" for describing the nine primary dementia risk factors (identified above). The prefix "iii" is used to designate secondary components in the dementia pathway.

As a client works thru the pathway of completing or qualifying for each component of the dementia category, he or she will then have a significant reduction in dementia risk. If and when a client fails out of the primary pathway due to poor results in testing, at times there will be a chance to again 're-enter' the pathway if certain criteria are reached.

Secondary pathways. These issues will add to the 'thickness of the rope,' as described above. If one or more of the individual dementia risk reduction factors is increased, there becomes a further distance between the client and his or her dementia risk. There are, for example, twenty four individual aspects that can be ranked, graded or tabulated or evaluated by the medical prevention center as part of the 'thickness of the rope'. Most of these aspects will be designated iii.1 thru iii.85, however some may simply be just pass or fail.

For each dementia risk factor included in the primary pathway, a person or organization performing the analysis of the present invention may have his or her own requirements for what must be recorded in a written report. For example, a reading of an ultrasound of the pancreas must include measurements of the pancreas at the head, body, and tail locations, with callout of all lesions, cysts, and findings. Currently, most of the radiological study results that are supplied to a doctor do not give this amount of detailed data. Often a report will include 'no obvious findings," "normal results," "nothing acute" or words that are a more of a generalization and not data. Data from testing for the present method must be provided based on specific data.

Some of the details that will go into a score (for all levels i, ii, and iii) will likely change over time. Therefore, scoring is somewhat dynamic. A fully developed scoring method may change over a number of years. Even then, as medicine and information change, findings that were considered bad may turn out to be not as bad as originally thought, as, for example, medical research advances. The ability for the score to remain dynamic on an annual basis is critical to success. Adjustments for current data from, for example, medical scientific papers, that provide additional research, are anticipated.

Figure 3:
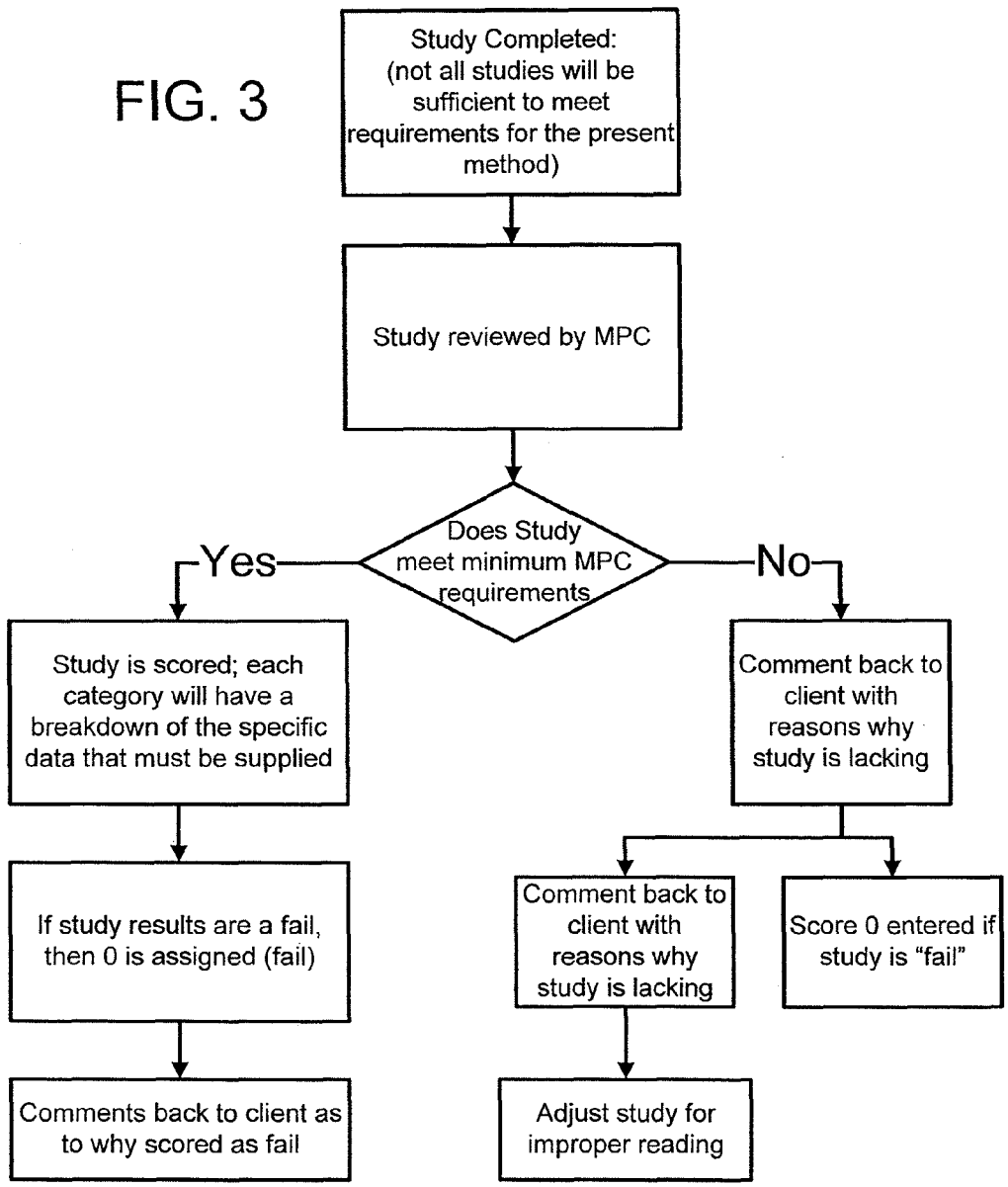
FIG. 3 is flowchart of an overall method for disease prevention of which the method for prevention of dementia of FIG. 1 is a component.

As can be seen in FIG. 3, the various studies performed are analyzed by a medical prevention center (designated MPC in the figures). The studies must meet minimum requirements of the medical prevention center. If the studies meet the minimum requirements, they are scored and assigned a score of 0 to 85. If the score is low or 0, the client is given comments as to why the study was scored as a fail with recommendations from increasing the score. If the studies do not meet the minimum requirements, comments are given to the client as to why and a 0 is entered as a score. If necessary, the study is adjusted if there was an improper reading.

Next, each of the nine dementia risk factors are analyzed, including brain tissue, atrial fibrillation, hypercoaguable state, LDL cholesterol, carotid artery evaluation, tobacco use, hypertension (HTN), diabetes mellitus, and systemic inflammation. Flowcharts for analysis are shown in FIG. 4 through FIG. 12.

The method of preventing dementia of the present invention can be expressed as an equation:

$$n = \frac{500}{4\pi a^2} + \frac{1000}{4\pi b^2} + \frac{1000}{4\pi g^2} + \frac{1100}{4\pi c^2} + \frac{600}{4\pi h^2} + \frac{900}{4\pi t^2} + \frac{800}{4\pi y^2} + \frac{900}{4\pi d^2} + \frac{400}{4\pi i^2} + \frac{1100}{4\pi x^2}$$

where:

n=integer used in risk of dementia score/final score. Expressed as a percent of chance to develop dementia in this client.

a=a value calculated from atrial fibrillation component.
b=a value calculated from brain tissue component.
g=a value calculated from LDL component.
c=a value calculated from carotids component.
h=a value calculated from hypercoaguable state component.
t=a value calculated from tobacco component.
y=a value calculated from hypertension component.
d=a value calculated from diabetes component.
i=a value calculated from systemic inflammation component.
x=a value calculated from secondary components.

The final number, "n" is rounded to an integer value that represents the chance of a client developing dementia. For example, if n=60, then there is approximately a 60 percent chance that that client will get dementia. If, for example, n=1.34, then the client has approximately a 1 percent chance of getting dementia. If n is any number over 100, n is rounded down to 100. Dementia is assured in the client.

Figure 4:
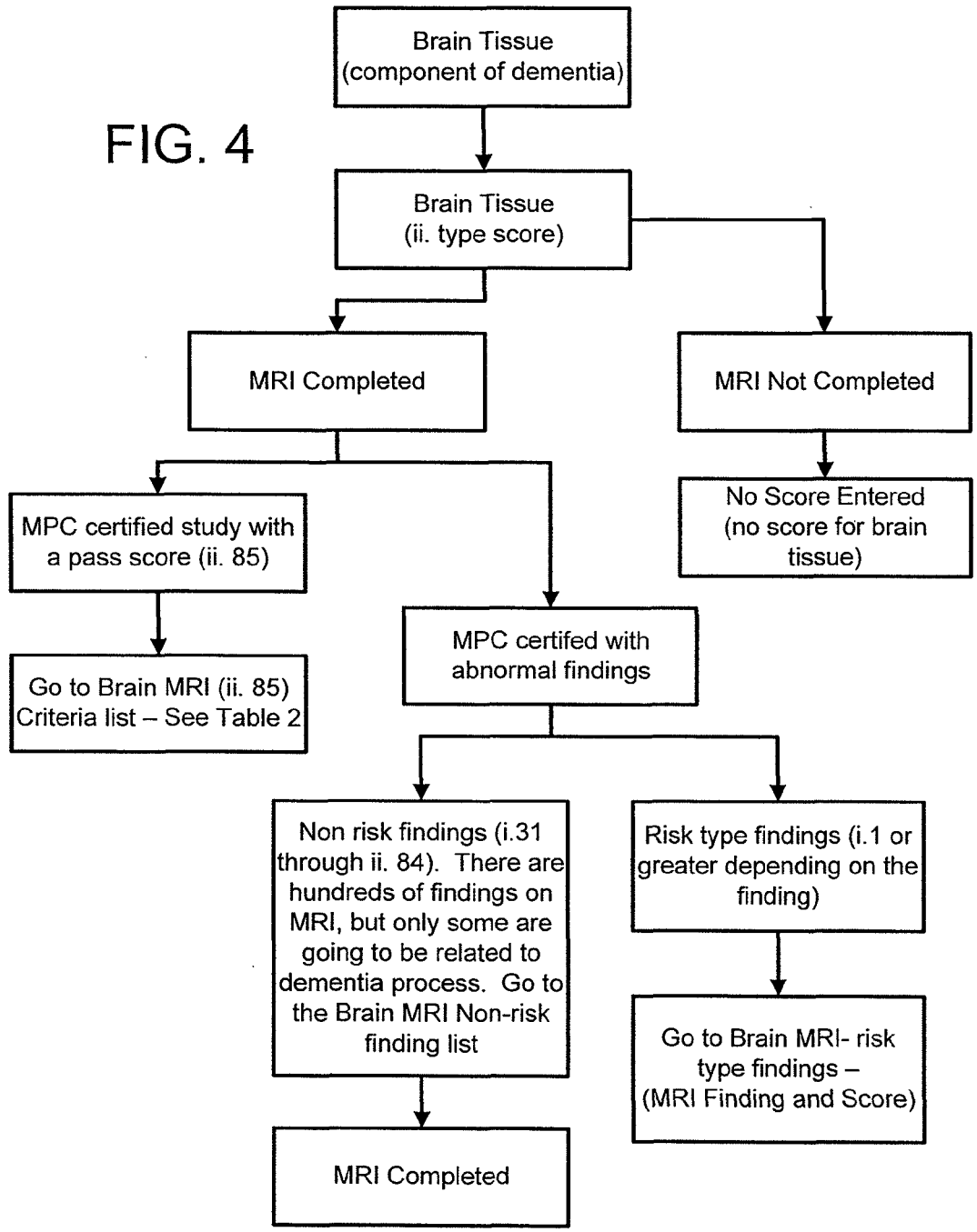
FIG. 4 is flowchart of a brain tissue component of the method of preventing dementia of FIG. 2.

Analyses for each of the dementia risk factors are discussed below:

Brain Tissue Risk Factor:

With respect to the brain tissue risk factor component, scoring (ii scoring) is shown in the flowchart of FIG. 4 and below. Scoring is from ii.0 to ii.85 based on the flowchart of FIG. 4 and the information below.

TABLE 2

| MRI findings and score. | NON-RISK | RISK | SCORE (ii.) |
|---|---|---|---|
| acoustic neuroma | X | | 60 |
| Alzheimer's disease | | X | 1 |

TABLE 2-continued

| MRI findings and score. | NON-RISK | RISK | SCORE (ii.) |
|---|---|---|---|
| Amyotrophic lateral sclerosis | | X | 11 |
| Aneurysm | | X | 30 |
| Arteriovenous cerebral malformation | | X | 40 |
| blood clot to brain | | X | 5 |
| brain abscess | X | | 5 |
| Tumor | | X | 1 |
| central pontine myelinolysis | | X | 1 |
| cerebral amyloid angiopathy | | X | 1 |
| subdural hematoma - acute | | X | 5 |
| subdural hematoma - chronic | | X | 5 |
| Cushing's disease | X | | 75 |
| Hypopituitarism | X | | 75 |
| Meniere's disease | X | | 60 |
| multiple sclerosis | | X | 2 |
| normal pressure hydrocephalus | | X | 2 |
| optic glioma | | X | 5 |
| pituitary tumor | X | | 50 |
| Prolactinoma | X | | 65 |
| stroke/TIA | | X | 1 |
| TMJ disorder | X | | 85 |
| Wilson's disease | | X | 1 |
| cavernous angioma | X | | 5 |
| arachnoid cyst | X | | 5 |
| Encephalitis | | X | 5 |
| Meningitis | X | | 68 |
| Parkinson's disease | | X | 8 |
| Atrophy | | X | 1 |
| Tuberculosis of brain | | X | 4 |
| Lewy-Bodies | | X | 1 |
| Ventriculitis | X | | 5 |
| Boreliosis | X | | 5 |
| Syphilis | X | | 5 |
| acute disseminated encephalomyelitis | | X | 2 |
| rhomben cephalitis | | X | 5 |
| Aspergillosis | | X | 4 |
| Blastomycosis | | X | 3 |
| herpes encephalitis | | X | 4 |
| Crytococcosis | | X | 2 |
| Cysticercosis | | X | 2 |
| fungal granulomatosis | | X | 2 |
| Histoplasmosis | | X | 1 |
| Creutzfeldt-Jakob disease | | X | 1 |
| Hughes Syndrome | | X | I |
| flair hyperintensities | | X | 1 |
| dilation of ventricles | X | | 6 |
| Demyelination | | X | 1 |
| cerebral aqueduct stenosis | X | | 5 |
| Coffin-Lowry Syndrome | | X | 5 |
| tuberous sclerosis | | X | 15 |
| any Prion brain disease | | X | 1 |
| subependymal nodule | | X | 20 |
| subependymal giant cell astrocytoma | | X | 1 |
| Joubert Syndrome | | X | 1 |
| cerebral palsy | | X | 2 |
| Von-Hippel-Lindau Syndrome | | X | 2 |
| trigeminal neuoralgia | X | | 25 |
| transverse myelitis | | X | 1 |
| Tay-Sachs disease | | X | 1 |
| subarachnoid hemorrhage | | X | 5 |
| Shy-Drager Syndrome | | X | 1 |
| Progressive Supranuclear palsy | | | 1 |
| motor neuron disease | X | | 15 |
| Guillian-Barre Syndrome | X | | 15 |
| Gaucher disease | | X | 1 |
| Friedreich's ataxia | | X | 10 |
| chronic inflammatory demyelinated polyneuropathy | | X | 1 |
| agenesis corpus callosum | X | | 10 |
| Chiara malformation | X | | 5 |
| Charcot-Marie-Tooth disorder | X | | 15 |
| brain cancer | | X | 1 |
| absence of the septum pellucidum | X | | 30 |
| Adrenoleukodystrophy | | X | 1 |
| Aicardi-Goutieres syndrome disorder | | X | 1 |
| neurological complications from AIDS | | X | 5 |
| Alexander Disease | | X | 2 |
| Alpers' Disease | | X | 2 |

TABLE 2-continued

| MRI findings and score. | NON-RISK | RISK | SCORE (ii.) |
|---|---|---|---|
| Angelman Syndrome | X | | 10 |
| bell's palsy | X | | 33 |
| benign intracranial hypertension | | X | 4 |
| Bradbury-Eggleston syndrome | | X | 1 |
| cerebral arteriosclerosis | | X | 1 |
| cerebellar degeneration | | X | 1 |
| cerebellar hypoplasia | | X | 1 |
| cerebral Beriberi | | X | 1 |
| cerebral giantism | | X | 1 |
| cerebral hypoxia | | X | 1 |
| cranial arteritis | | X | 3 |
| Craniosynostosis | X | | 5 |
| Dandy-Walker Syndrome | X | | 5 |
| Lennox-Gastaut Syndrome | | X | 2 |
| Leukodystrophy | | X | 2 |
| Lissencephaly | X | | 5 |
| Machado-Joseph disease | | X | 2 |
| Macroencephaly | X | | 40 |
| Microcephaly | X | | 40 |
| moyamoya disease | | X | 2 |
| neuronal migration disorders | | X | 1 |
| Neurosarcoidosis | | X | 1 |
| Niemann-Pick disease | | X | 1 |
| Pelizaeus-Merzbacher disease | | X | 1 |
| periventricular leukomalacia | | X | 1 |
| Porencephaly | X | | 1 |
| Etc. | | | |

Example of "Brain MRI Criteria" for Getting a (ii.85) Score:
  No movement artifact
  If movement artifact the study needs to be repeated
  Brain structures are identified (this insures that the radiologist did read the study)
  Pituitary with comment
  White matter changes are identified
  Size, location, and configuration are identified.
  No wording such as 'age related' or 'age appropriate' are able to be used.
  No wording of "age related" findings are able to appear on the report.
  Etc.

Example of "Brain—Non Risk Findings" for Getting a (ii.) Score:
  Arnold Chiari malformation
    A common variant of the brain that will not apply to the Dementia pathway. It consists of a downward displacement of the cerebellar tonsils through the foramen magnum (the opening at the base of the skull), sometimes causing non-communicating hydrocephalus as a result of obstruction of cerebrospinal fluid (CSF). The cerebrospinal fluid outflow is caused by phase difference in outflow and influx of blood in the vasculature of the brain. It can cause headaches, fatigue, muscle weakness in the head and face, difficulty swallowing, dizziness, nausea, impaired coordination, and, in severe cases, paralysis.
  Sinus disease
  Cervical neck arthritis
  Facial soft tissue findings
  A variety of pituitary findings
  Small adnoma
  Empty sella syndrome
  Specific scores are applied in the above charts.

Example of "Brain MRI RISK TYPE FINDINGS" for Getting a (ii.) Score:
  White matter changes
    White matter changes are at the primary concern of what is related to the dementia process.
    The number, size, and configuration of white matter changes will develop the score.
      Example—many white matter changes through the brain will give (ii.1) score
  Evidence of stroke
  Evidence of ischemic disease
  Intra cranial calcifications
  Metastatic brain disease
  Tumor of the brain
  Other than simple tumor of the pituitary (such as an adnoma)
  Carotid artery disease
  Posterior circulation disease
  Gross trauma of brain tissue
  Severe developmental abnormality
  Etc. All the above give a very low score or an ii.1 (fail)

Figure 5:
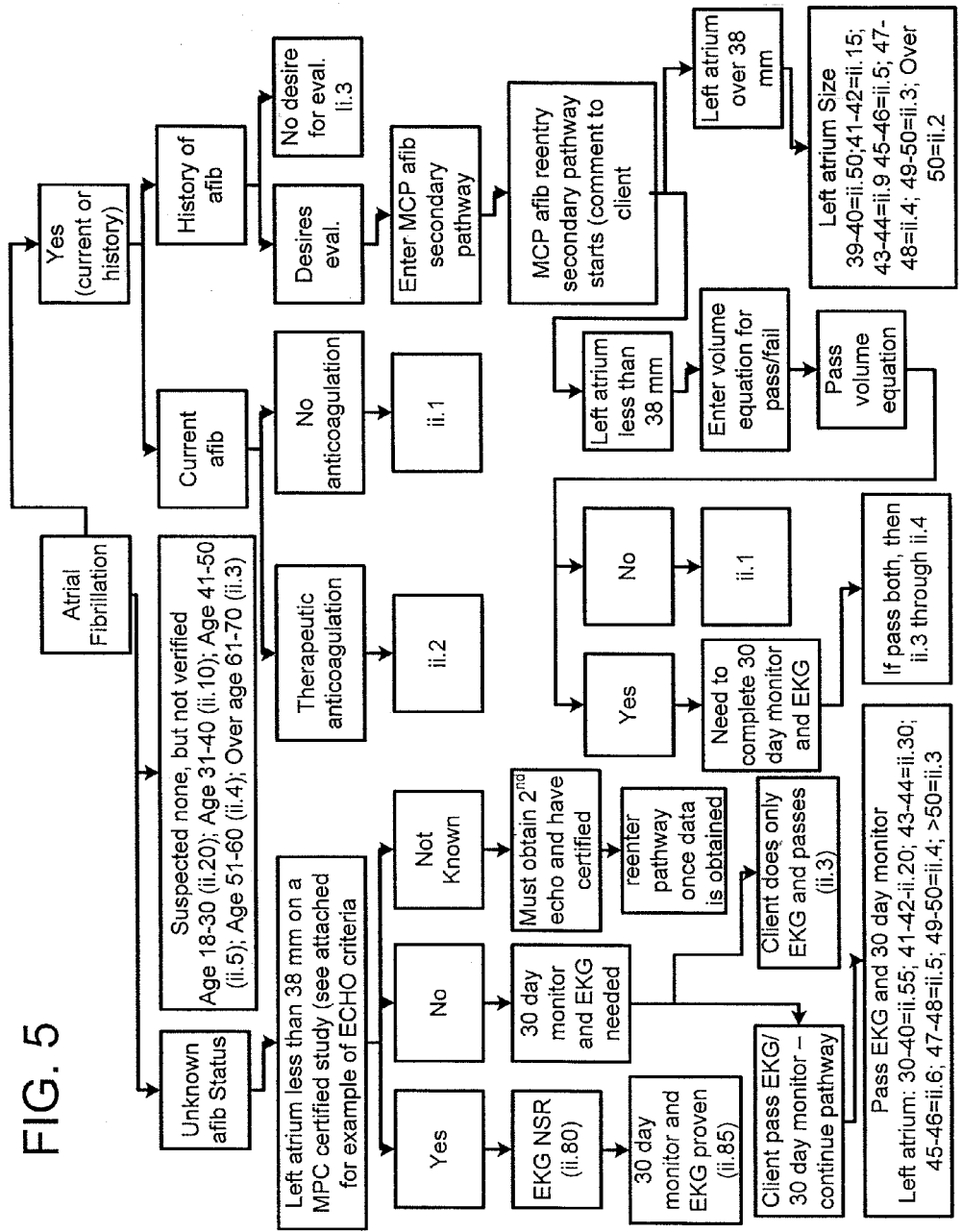
FIG. 5 is flowchart of an atrial fibrillation component of the method of preventing dementia of FIG. 2.

Atrial Fibrillation Risk Factor:
  With respect to the atrial fibrillation risk factor component, scoring (ii scoring) is shown in the flowchart of FIG. 5 and as follows. Score determinations are shown in the flowchart of FIG. 5.
  Example of "2d Echo Criteria" for Getting a (ii.) Score:
    Measurement in millimeters of left atrium at max dimension
    Measurement of thickness of septum
    Measurement of thickness of posterior wall
    Estimation of the ejection fraction of the heart
    Measurement of the left ventricle end diastolic size
    Measurement of the right ventricle end diastolic size
    Measurement of the heart in max diameter at end of systole
    Measurement of the heart in maximum diameter at the end of diastolic phase
    Full description of each heart valve
    Doppler flow description of each valve
    Calculation of any aortic stenosis by area
    Reporting of velocities across each valve
    Etc.

Figure 6:
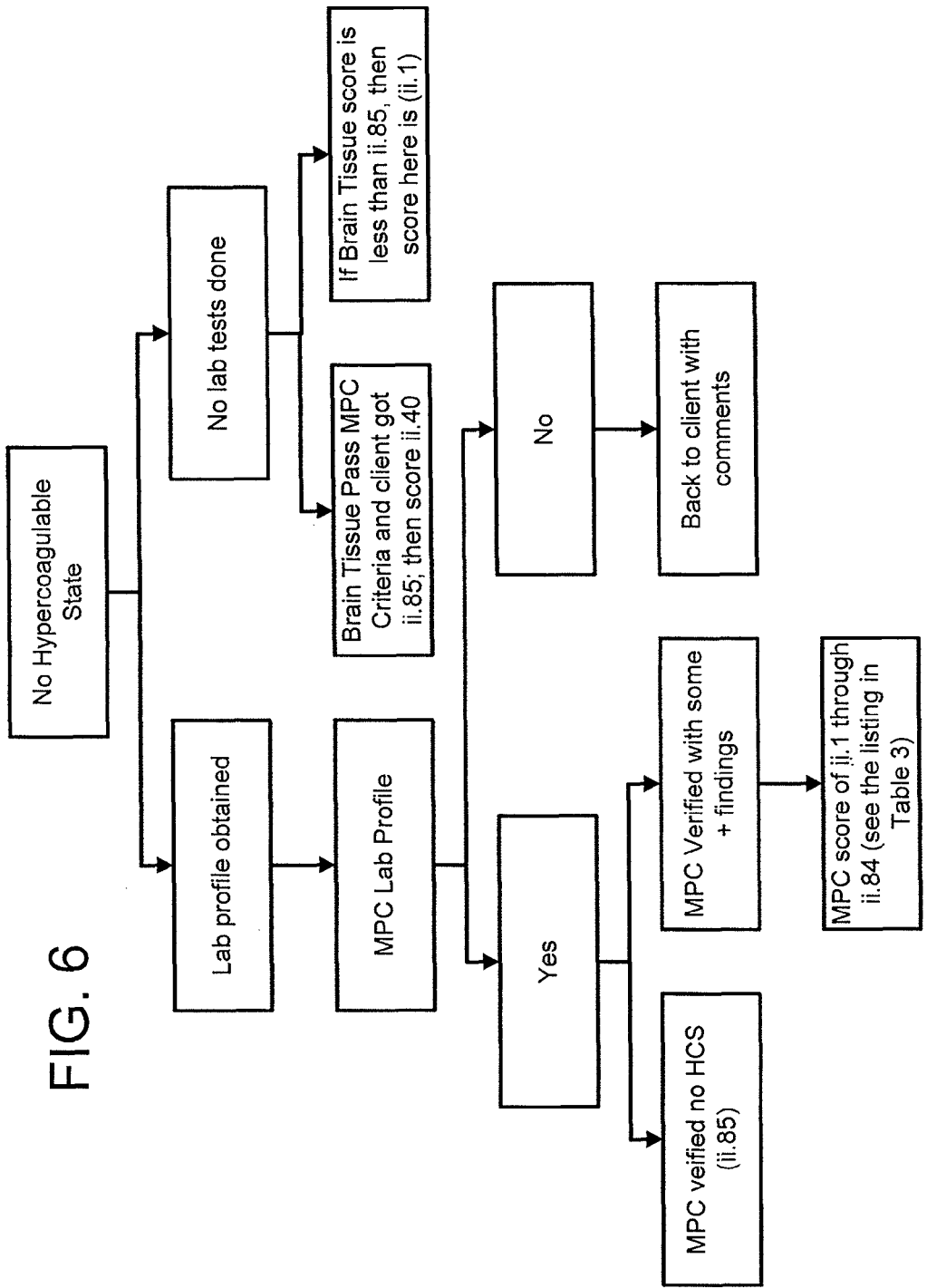
FIG. 6 is flowchart of a hypercoaguable state component of the method of preventing dementia of FIG. 2.

Hypercoaguable State Component:
  With respect to the hypercoaguable state risk factor component, scoring (ii scoring) is shown in the flowchart of FIG. 6 and below. Scores are determined using the flowchart of FIG. 6 and Table 3, below.

TABLE 3

| hypercoaguable state component - detailed explanation below | Score (ii.) |
|---|---|
| Prothrombin (INR) 0.7 thru 1.3 | ii.85 |
| Prothrombin (INR) 1.4 thru 1.9 | ii.10 |
| Prothrombin (INR) 2.0 and over | ii.2 |
| PTT (Partial Thromboplastin Time): less than 24 | ii.5 |
| PTT (Partial Thromboplastin Time): 24-33 | ii.85 |
| PTT (Partial Thromboplastin Time): over 33 | ii.4 |
| Homocysteine LEVEL: 0-6 | ii.85 |
| Homocysteine LEVEL: 7-13 | ii.20 |
| Homocysteine LEVEL: over 13 | ii.2 |
| Lactic Acid 0 to 2.0 | ii.85 |
| Lactic Acid 2.1 to 3 | ii.2 |
| Lactic Acid over 3.1 | ii.I |
| Antithrombin III Activity less than 80 percent | ii.2 |
| Protein C Activity: less than 70 percent | ii.2 |
| Protein S Activity: less than 70 percent | ii.2 |
| Antiphospholipid Antibody Cardiolipin Antibody IgG: less than 10 | ii.85 |
| Antiphospholipid Antibody Cardiolipin Antibody IgG: 10-15 | ii.50 |

TABLE 3-continued

| hypercoaguable state component - detailed explanation below | Score (ii.) |
|---|---|
| Antiphospholipid Antibody Cardiolipin Antibody IgG: 16-40 | ii.20 |
| Antiphospholipid Antibody Cardiolipin Antibody IgG: over 40 | ii.3 |
| Antiphospholipid Antibody Cardiolipin Antibody IgA LESS THAN 10 | ii.85 |
| Antiphospholipid Antibody Cardiolipin Antibody IgA 10-15 | ii.20 |
| Antiphospholipid Antibody Cardiolipin Antibody IgA OVER 15 | ii.3 |
| Antiphospholipid Antibody Cardiolipin Antibody IgM less than 10 | ii.85 |
| Antiphospholipid Antibody Cardiolipin Antibody IgM 10-15 | ii.8 |
| Antiphospholipid Antibody Cardiolipin Antibody IgM 15-40 | ii.2 |
| Antiphospholipid Antibody Cardiolipin Antibody IgM over 40 | ii.1 |
| Prothrombin Gene Mutation: single copy | ii.2 |
| Prothrombin Gene Mutation: double copy mutation | ii.1 |
| Factor V Leiden - homozygous | ii.1 |
| Factor V Leiden - heterozygous | ii.2 |
| Methylenetetrahydrofolate Reductase (MTHFR) homozygous: C677T | ii.2 |
| MTHFR heterozygous C677T | ii.3 |
| MTHFR heterozygous A1298C | ii.10 |
| MTHFR homozygous A1298C | ii.7 |
| Phosphatidylserine (IgG): Less than 10 | ii.85 |
| Phosphatidylserine (IgG): 10-20 | ii.7 |
| Phosphatidylserine (IgG): Over 20 | ii.2 |
| Phosphatidylserine (IgA): Less than 20 | ii.85 |
| Phosphatidylserine (IgA): 20-30 | ii.8 |
| Phosphatidylserine (IgA): Over 30 | ii.2 |
| Phosphatidylserine (IgM): Less than 25 | ii.85 |
| Phosphatidylserine (IgM): 25-30 | ii.10 |
| Phosphatidylserine (IgM): Over 30 | ii.2 |

Additional definitions of specific markers:

Prothrombin: a blood test that measures how long it takes your blood to clot; measured in seconds; reference range 9.9-11.6

INR (international normalized ratio): a blood test that measures the time it takes for blood to clot; the higher the number the longer it takes for the blood to clot; used in monitoring anticoagulant medications; in a healthy person their INR is 1.0 and for people on anticoagulation therapy it should be between 2.0 and 3.0.

PTT (Partial Thromboplastin Time): a blood test that measures the time it takes for blood to clot; A phlebotomist collects blood samples in vacu-tubes with oxalate or citrate to arrest coagulation by binding calcium. The specimen is then delivered to the laboratory. In order to activate the intrinsic pathway, phospholipid, an activator (such as silica, celite, kaolin, ellagic acid), and calcium (to reverse the anticoagulant effect of the oxalate) are mixed into the plasma sample. The time is measured until a thrombus (clot) forms; measured in seconds; reference range 25.0-31.3

Homocysteine: a blood test to determine if a client has a B-12 or folate deficiency; reference range 3.7-13.9

Lactic Acid: a blood test that measures the level of lactic acid made in the body mainly made by muscle tissue and red blood cells; when the oxygen level in the body is normal, carbohydrate breaks down into water and carbon dioxide; when the oxygen level is low, carbohydrate breaks down for energy and makes lactic acid; reference range 0.7-2.1

Antithrombin III Activity: synthesized in liver and endothelial cells and acts as an anticoagulant by directly binding and inactivating the serine proteases (Factors XIa, IXa, Xa, and Thrombin); measured in % of activity; reference range 80-120%

Protein C Activity: Protein C deficiency is caused by mutations in the PROC gene. This gene provides instructions for making protein C, which is found in the bloodstream and is important for controlling blood clotting. Protein C blocks the activity of (inactivates) certain proteins that promote blood clotting. Most of the mutations that cause protein C deficiency change single protein building blocks (amino acids) in protein C, which disrupts its ability to control blood clotting. Individuals with this condition do not have enough functional protein C to inactivate clotting proteins, which results in the increased risk of developing abnormal blood clots. Protein C deficiency can be divided into type I and type II based on how mutations in the PROC gene affect protein C; measured in percent of normal; reference range 70-180%

Protein S Activity: Protein S deficiency is caused by mutations in the PROS1 gene. This gene provides instructions for making protein S which is found in the bloodstream and is important for controlling blood clotting. Protein S blocks the activity of (inactivates) certain proteins that promote blood clotting. Most of the mutations that cause protein S deficiency change single protein building blocks (amino acids) in protein S, which disrupts its ability to control blood clotting. Individuals with this condition do not have enough functional protein S to inactivate clotting proteins, which results in the increased risk of developing abnormal blood clots. Protein S deficiency can be divided into type I and type II based on how mutations in the PROS1 gene affect protein S; measured in percent of normal; reference range 70-180%

Antiphospholipid Antibody Panel: The antiphospholipid syndrome is a disorder of the immune system that is characterized by excessive clotting of blood and/or certain complications of pregnancy (premature miscarriages, unexplained fetal death, or premature birth) and the presence of antiphospholipid antibodies (cardiolipin or lupus anticoagulant antibodies) in the blood. Clients with antiphospholipid syndrome have developed abnormal symptoms while having antiphospholipid antibodies that are detectable with blood testing. Includes the following testing:

Cardiolipin Antibody: to help investigate inappropriate blood clot formation, to help determine the cause of recurrent miscarriage, or as part of an evaluation for Antiphospholipid Syndrome; see reference ranges below:

Cardiolipin Ab (IgG):
<10 GPL U/mL Negative
10-15 GPL U/mL Equivocal
16-40 GPL U mL Positive-Uncertain risk factor; may be reactive
>40 GPL U m/L Positive-Risk factor for thrombosis and pregnancy loss Cardiolipin Ab (IgA):
<10 APL U m/L Negative
10-15 APL U m/L Equivocal
>15 APL U m/L Positive Cardiolipin Ab (IgM):
<10 MPL U m/L Negative
10-15 MPL U m/L Equivocal
16-40 MPL U m/L Positive-Uncertain risk factor; may be reactive
>40 MPL U m/L Positive-Risk factor for thrombosis and pregnancy loss Phosphatidylserine (IgG, IgA, IgM): Phosphatidylserine is found in the membranes of platelets and endothelial cells, which participate in the coagulation cascade. Due to its physiologic role, testing for autoantibodies directed towards phosphatidylserine provides not only more relevant results, but also additional information to assess the risk of thrombosis. See reference range below.

Phosphatidylserine (IgG):
<10 U m/L Negative
10-20 U/mL Equivocal—Found in small percentage of the healthy population; may be reactive
>20 U/mL Positive—Risk factor for thrombosis and pregnancy loss.
Phosphatidylserine (IgM):
<25 U m/L Negative
25-35 U/mL Equivocal—Found in small percentage of the healthy population; may be reactive
>35 U/mL Positive—Risk factor for thrombosis and pregnancy loss.
Phosphatidylserine (IgA):
<20 U m/L Negative
20-30 U/mL Equivocal—Found in small percentage of the healthy population; may be reactive
>30 U/mL Positive—Risk factor for thrombosis and pregnancy loss.

The Antiphospholipid Antibody Syndrome (APS) is a clinical-pathologic correlation that includes a clinical event (e.g. thrombosis, pregnancy loss, thrombocytopenia) and persistent positive Antiphospholipid Antibodies (IgM or IgG ACA>40 MPL/GPL, IgM or IgG anti-B2GPI antibodies, or a Lupus Anticoagulant). The IgA isotype has been implicated in smaller studies, but have not yet been incorporated into the APS criteria. International consensus guidelines suggest waiting at least 12 weeks before retesting to confirm antibody persistence. Reference: J Thromb Haemost 2006: 4; 295.

Beta2-Glycoprotein (IgA, IgM, IgG): a protein involved in the regulation of the coagulation system: reference range <=20 SAU, SMU, SGU accordingly Prothrombin Gene Analysis: reference range positive vs negative. This negative result does not rule out the presence of other mutations within the Prothrombin/Factor II gene or other causes of thrombophilia. The G20210A mutation in the Prothrombin (Factor gene is the second most common inherited risk factor for thrombosis. Individuals who have one copy of the mutation are at a 3-6 fold increased risk for thrombosis and individuals who have two copies are at an even more increased risk. The G20210A mutation is detected by signal amplification of the Prothrombin (Factor IT) gene by allele-specific hybridizations and fluorescent detection of hybridized probes. Since genetic variation and other factors can affect the accuracy of direct mutation testing, the results should be interpreted in light of clinical and familial data.

Factor V Leiden: reference range positive vs. negative. A negative result does not rule out the presence of other mutations within the Factor V gene or other causes of thrombophilia. Factor V Leiden is one of the most common causes of inherited thrombophilia. The R506Q mutation leads to resistance to degradation of the Factor V protein by activated protein C (APC). Individuals who have one copy of the mutation are at a 4-8 fold increased risk of thrombosis and individuals who have two copies are at a 50-100 fold increased risk. The R506Q mutation is detected by signal amplification of the Factor V gene by allele-specific hybridizations and chemiluminescent detection of hybridized probes. Since genetic variation and other factors can affect the accuracy of direct mutation testing, these results should be interpreted in light of clinical and familial data.

Methylenetetrahydrofolate Reductase (MTHFR): reference range positive vs. negative. A positive result has been associated with an increased risk for hyperhomocysteinemia and vascular diseases. There have been rare reports where the C677T and A1298C mutations are on the same chromosome, however the clinical significance of this is not well understood. This test cannot determine whether each mutation is on the same (cis) or different (trans) chromosomes. This can only be determined by testing the parents of the client. If the parents are unavailable, other close family members may be helpful. Until further information is available, care should be taken regarding the medical management of these individuals. Consider genetic counseling and DNA testing for at-risk family members. Hyperhomocysteinemia is a risk factor for arterial disease and venous thrombosis. Homocysteine levels are affected by nutritional and genetic factors. Since MTHFR is involved in methylation of homocysteine to methionine, individuals with MTHFR gene mutations that reduce enzyme activity may develop hyperhomcysteinemia and thus be at elevated risk for vascular disease. The C677T and A1298C mutations are detected by signal amplification of the MTHFR gene by allele-specific hybridizations and fluorescent detection of hybridized probes. Since genetic variation and other factors can affect the accuracy of direct mutation testing, these results should be interpreted in light of clinical and familial data.

Example of "Hypercoaguable State Evaluation" for Getting a (ii.) Score:
  PT/INR,
  PTT,
  Bleeding Time,
  Factor V Leiden,
  Anti-thrombin 3,
  Protein C,
  Protein S,
  Homocystine Level,
  Lactate,
  ANA,
  Pyruvate
  MTHFR (Methylenetetrahydrofolate reductase) gene mutation,
  Antiphospholipid antibody
  Anti-Cardiolipin,
  Factor II gene mutation.

Figure 7:
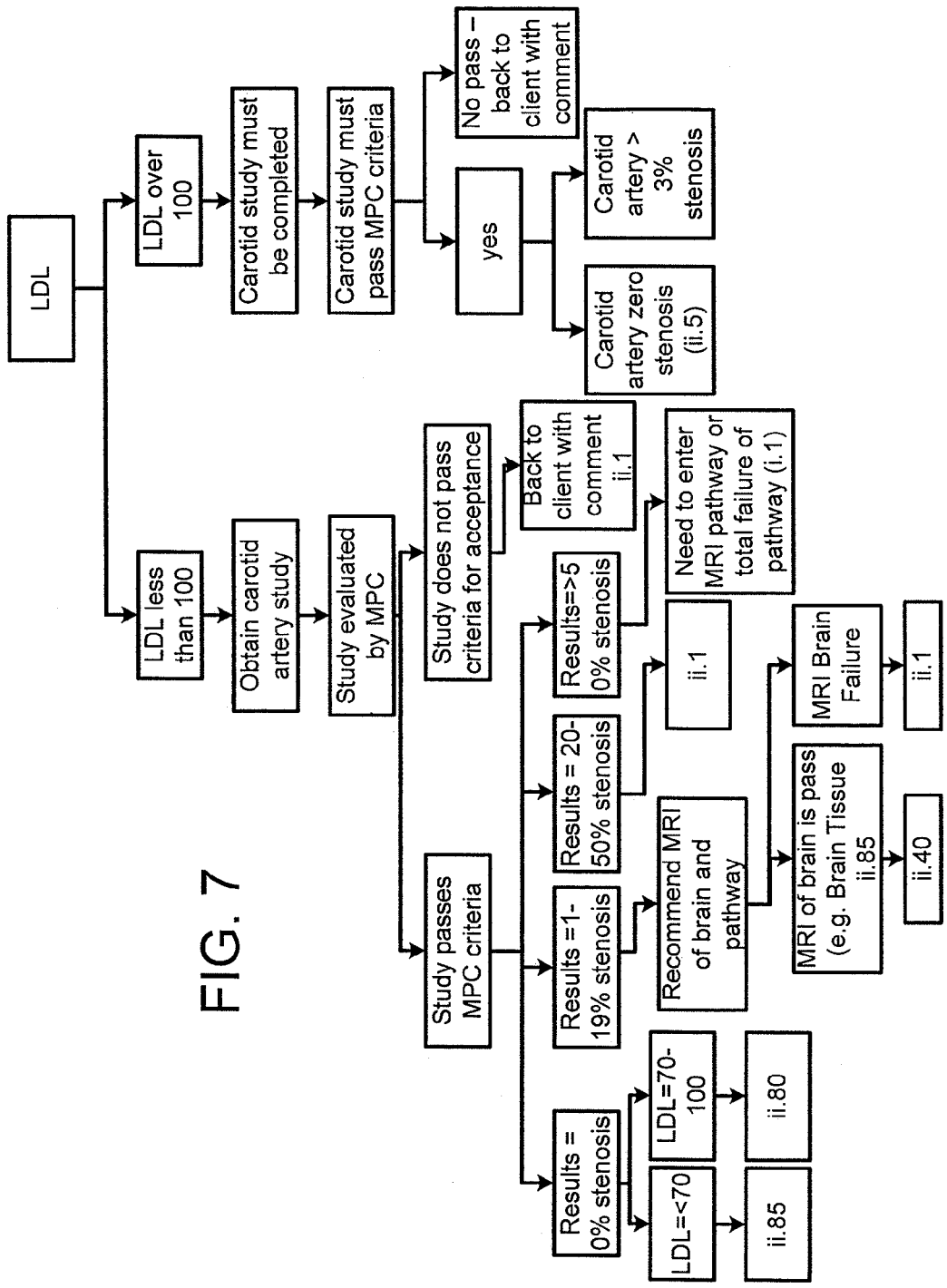
FIG. 7 is flowchart of an LDL cholesterol component of the method of preventing dementia of FIG. 2.

LDL Cholesterol Risk Factor:
  With respect to the LDL cholesterol risk factor component, scoring (ii scoring) is shown in the flowchart of FIG. 7. LDL testing, a carotid artery study, and possibly and MRI of the brain must be performed, as noted.

Figure 8:
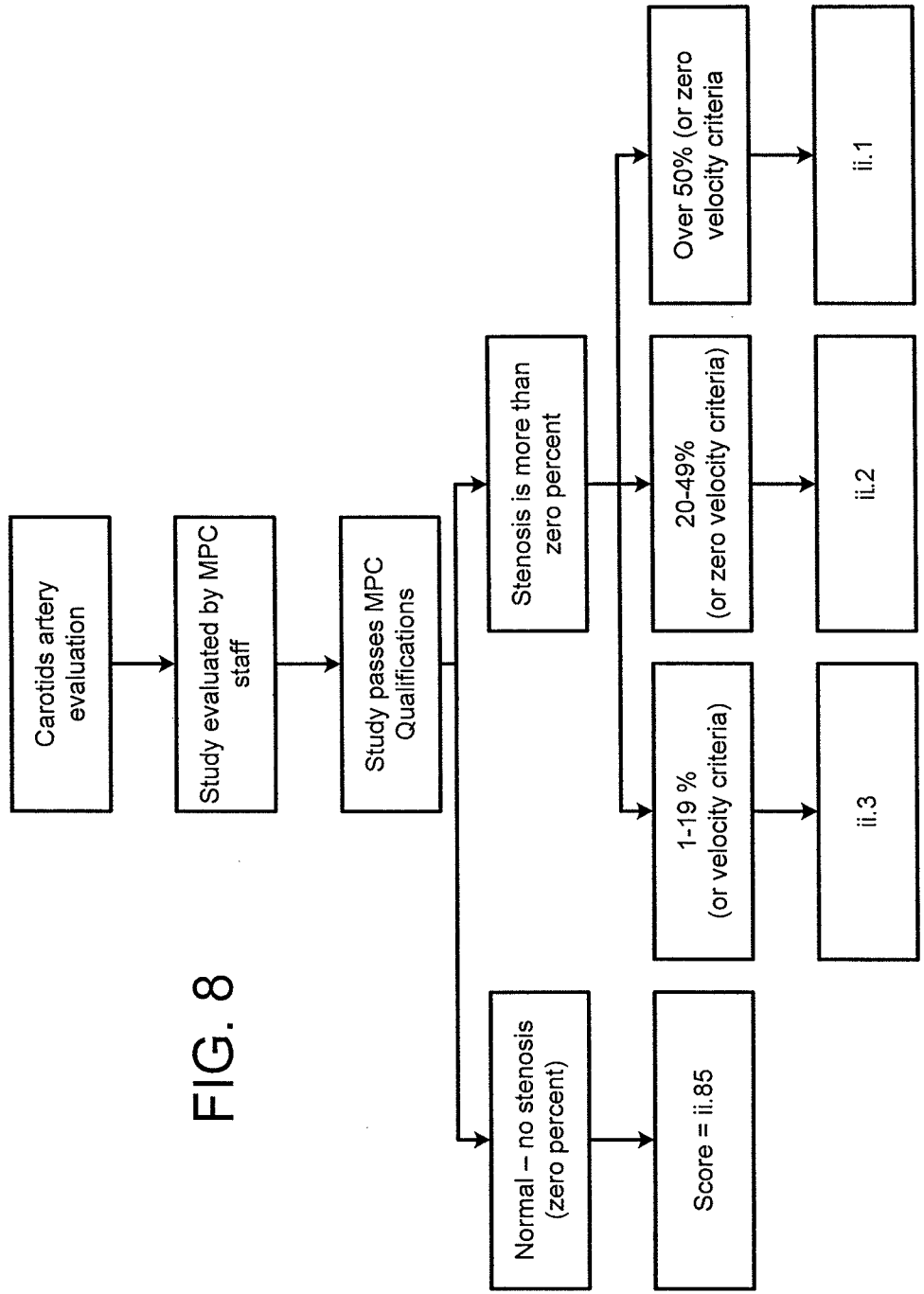
FIG. 8 is flowchart of a carotid artery evaluation component of the method of preventing dementia of FIG. 2.

Carotid Artery Stenosis Risk Factor:
  With respect to the carotid artery risk factor component, scoring (ii scoring) is shown in the flowchart of FIG. 8. Scoring is shown in the flowchart of FIG. 8.

Figure 9:
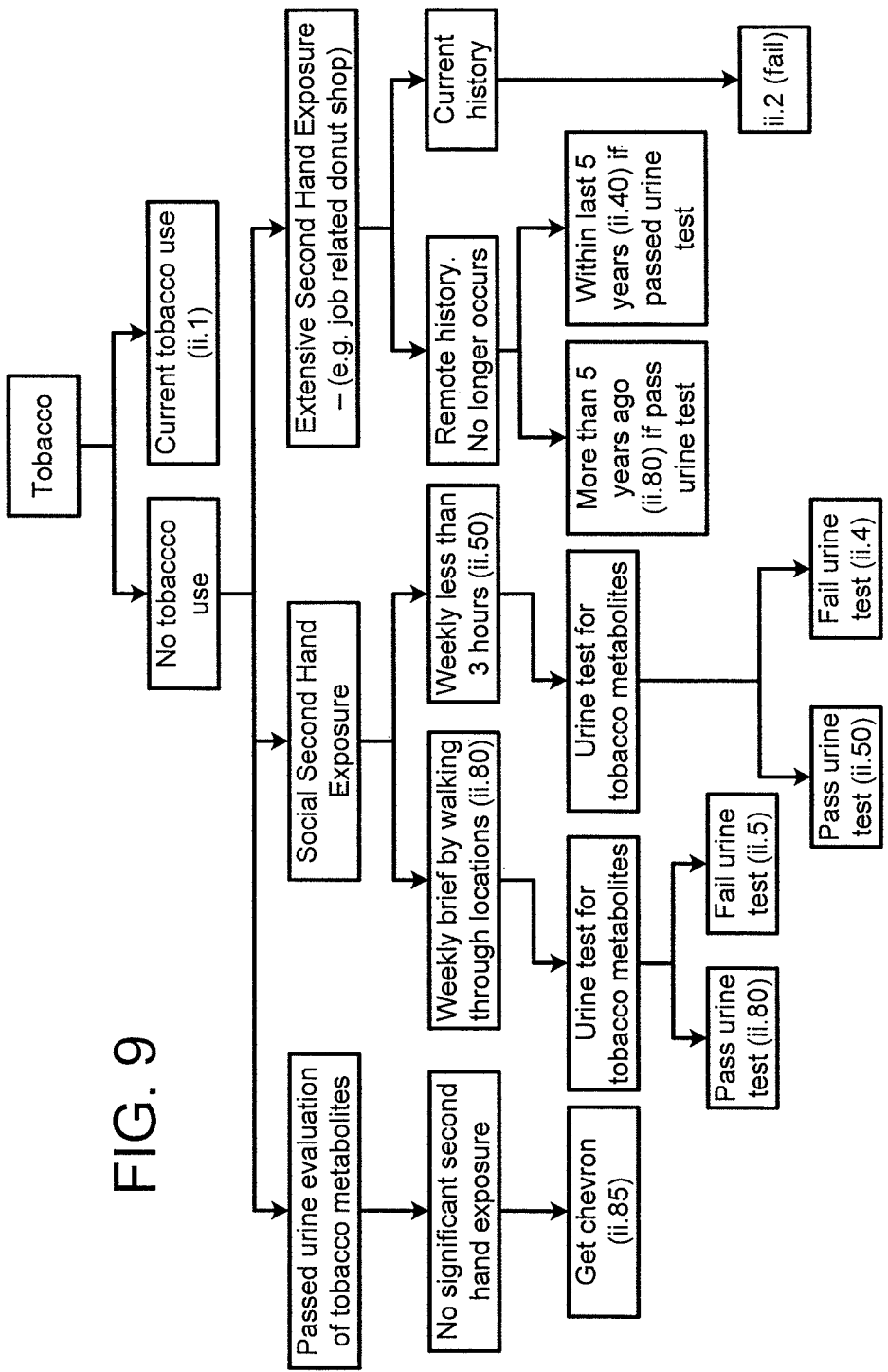
FIG. 9 is flowchart a tobacco use component of the method of preventing dementia of FIG. 2.

Tobacco Risk Factor:
  With respect to the tobacco risk factor component, scoring (ii scoring) is shown in the flowchart of FIG. 9. For purposes of the present invention, 100 cigarettes over a lifetime is considered that the client has had tobacco use/tobacco exposure. 100 cigarettes puts the client into the branch of a prior tobacco user. Evaluation of current tobacco use is done by a urine test that a client would have to pass to prove that they do not use tobacco. Scoring is shown in the flowchart of FIG. 9.

Figure 10:
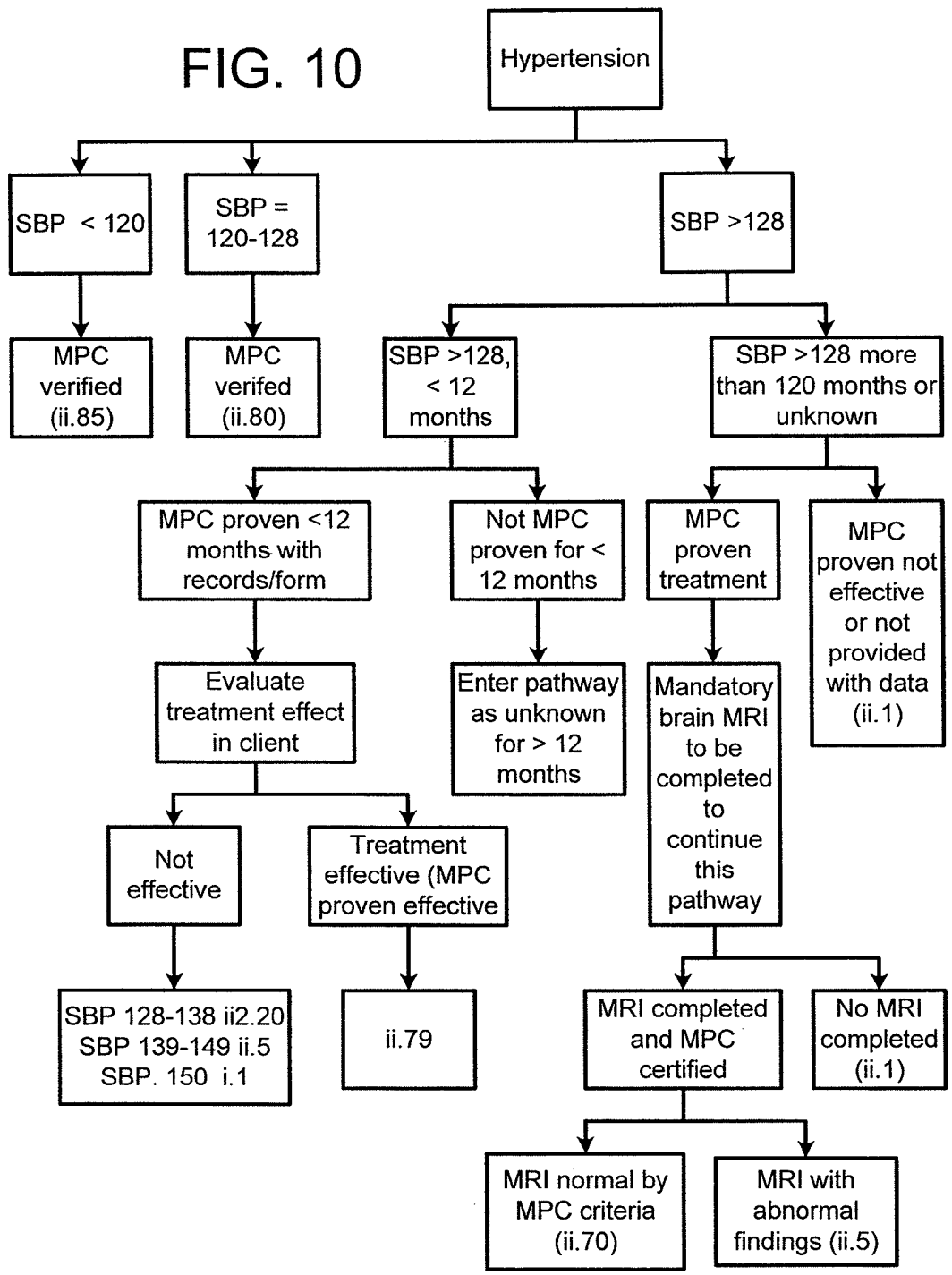
FIG. 10 is flowchart of an HTN component of the method of preventing dementia of FIG. 2.
Figure 11:
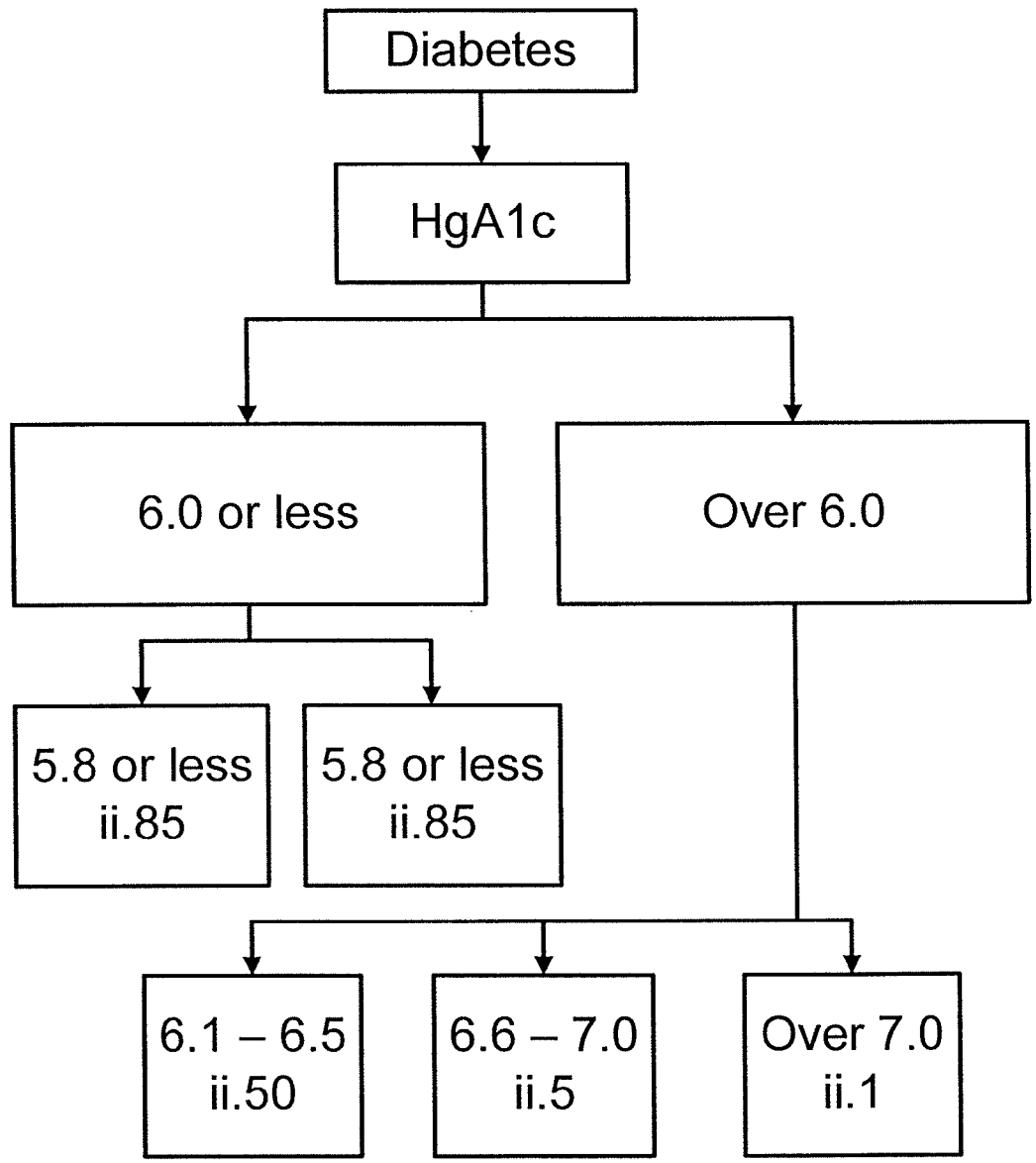
FIG. 11 is a flowchart of a diabetes evaluation component of the method of preventing dementia of FIG. 2.

Hypertension (HTN) Risk Factor:
  With respect to the hypertension risk factor component, scoring (ii scoring) is shown in FIG. 10. Scoring is shown in the flowchart of FIG. 10.
    Proving that treatment is effective includes:
    Client will have form indicating the blood pressure recordings.
    Data from the completed form will provide the information for the medical prevention center to then provide the score Diabetes Risk Factor:

With respect to the diabetes risk factor component, scoring (ii scoring) is shown in the flowchart of FIG. 11. HgA1c, glycated hemoglobin (hemoglobin A1c, $HbA_{1c}$, A1C, or $Hb_{1c}$) is a form of hemoglobin which is measured primarily to identify the average plasma glucose concentration over time. It is formed in a non-enzymatic glycation pathway by hemoglobin's exposure to plasma glucose. Normal levels of glucose produce a normal amount of glycated hemoglobin. As the average amount of plasma glucose increases, the fraction for glycated hemoglobin increases in a predictable way. This serves as a marker of blood sugar levels. The previous month's average blood sugar levels will affect the measurement. Commercially available lab tests vary widely.

Figure 12:
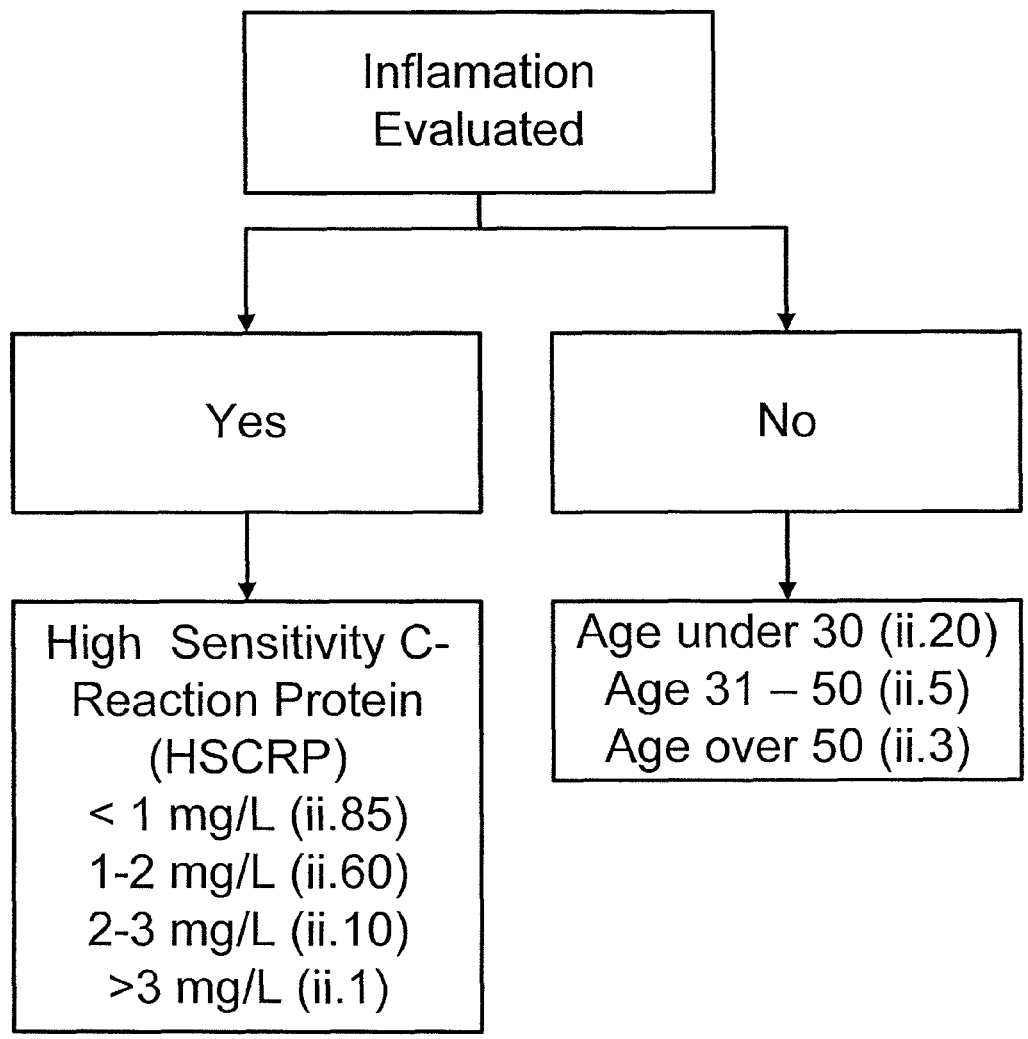
FIG. 12 is flowchart of an inflammation evaluation component of the method of preventing dementia of FIG. 2.

Systemic Inflammation Risk Factor:

With respect to the systemic inflammation risk factor component, scoring (ii scoring) is shown in the flowchart of FIG. 12. High Sensitivity (also called Ultra-sensitive) C-reactive protein is known as HS-CRP, US-CRP or CRP for short. It is a protein found in the blood and what we call a "marker" for inflammation, meaning its presence indicates a heightened state of inflammation in the body. Inflammation is a normal response to many physical states including fever, injury and infection. Inflammation plays a role in the initiation and progression of cardiovascular disease. HS-CRP can be completed by commercially available labs (such as the Cholestech LDX® System).

Secondary Risk Factors:

Secondary Components score (z) is obtained by totaling the assigned score for each secondary component. The results will be used to calculate (x).

While in this section a higher integer is worse, the final equation will convert the total "z" into a similar final score "x", that can then be used in the main dementia equation.

TABLE 4

| # | Secondary component | score |
|---|---|---|
| 1 | History of cancer with suboptimal treatment | 50 |
| 2 | Carbon monoxide exposure massive | 84 |
| 2 | Carbon monoxide exposure minimal | 70 |
| 3 | Low oxygen exposure | 70 |
| 4 | Brain anoxia under 10 min. | 50 |
| 4 | Brain anoxia over 10 min. | 84 |
| 5 | Brain shock, single event due to trauma | 50 |
| 5 | Brain shock, multiple event due to trauma | 84 |
| 5 | Brain shock, multiple event due to lifestyle (boxing/motocross/concussions) | 84 |
| 6 | Critical Low Hemoglobin 6.0 to 7.0 | 83 |
| 6 | Critical low hemoglobin less than 6.0 | 84 |
| 7 | Retinal artery occlusion (a cherry red spot) | 84 |
| 8 | Obstructive sleep apnea, mild requiring treatment | 50 |
| 8 | Obstructive sleep apnea, moderate requiring treatment | 75 |
| 8 | Obstructive sleep apnea, severe requiring treatment. | 83 |
| 9 | EKG with ischemic changes (ST changes) | 83 |
| 10 | Failure of a treadmill or chemical stress test | 83 |
| 11 | No aspirin use in male over 40 and female over 50 | 50 |
| 12 | Rheumatoid arthritis verified with (ccp rf -) | 55 |
| 13 | Low HDL less than 10 | 80 |
| 13 | Low HDL 10 to 15 | 70 |
| 13 | Low HDL 16-20 | 60 |
| 13 | Low HDL 21-25 | 50 |
| 13 | Low HDL 26-30 | 40 |
| 13 | Low HDL 31-35 | 30 |
| 13 | Low HDL 36-40 | 20 |
| 14 | High HDL 50 and over | −10 |
| 15 | LDL less than 70 | −20 |
| 16 | Sickle cell disease | 55 |
| 17 | Mitral valve heart disease moderate disease | 55 |
| 17 | Mitral valve heart disease severe disease | 75 |
| 17 | Aortic valve heart disease moderate disease | 68 |
| 17 | Aortic valve heart disease severe disease | 82 |
| 18 | Baseline normal neuropsychiatric evaluation | −40 |
| 19 | Overnight hypoxia to Pa02 less than 76 | 55 |
| 19 | Overnight hypoxia to Pa02 77 to 82 | 40 |
| 19 | Overnight hypoxia to Pa02 83 to 87 | 10 |
| 20 | Nephritic syndrome | 70 |
| 21 | Nephritic syndrome | 80 |
| 22 | Presence of systemic lupus of any organ/system (SLE) | 80 |
| 23 | Presence of anti ribosomal P Protein | 83 |
| 24 | Microvascular eye disease mild | 80 |
| 24 | Microvascular eye disease moderate | 82 |
| 24 | Microvascular eye disease severe | 84 |
| 25 | History of disseminate intravascular coagulation | 80 |
| 26 | History of thrombotic thrombocytic purpura | 80 |
| 27 | History of Idiopathic Thrombocytopenic Purpura (ITP) | 80 |
| 28 | Creatinine elevated 1.6 to 1.9 | 80 |
| 28 | Creatinine elevated 2.0 to 3.0 | 83 |
| 28 | Creatinine elevated over 3.1 | 84 |
| | Total = z | (total score) |

Total number=z (range −70 to <600)

x=85−z

Where x must be a number 1 or greater, but less than 85

X in the dementia equation, above

Finally, the score for each of these nine risk factors is applied to the equation below (as described above).

$$n = \frac{500}{4\pi a^2} + \frac{1000}{4\pi b^2} + \frac{1000}{4\pi g^2} + \frac{1100}{4\pi c^2} + \frac{600}{4\pi h^2} + \frac{900}{4\pi t^2} + \frac{800}{4\pi y^2} + \frac{900}{4\pi d^2} + \frac{400}{4\pi i^2} + \frac{1100}{4\pi x^2}$$

The resulting number, n, is the risk of dementia score. The client is advised how to lower this final score by lowering one or more scores in each of the nine dementia risk factors. Lowering scores in each of these risk factors is well known.

DEFINITIONS

For purposes of the present method, the following definitions apply:

Brain: the portion of the central nervous system that is enclosed in the cranium, continuous with the spinal, and composed of gray matter and white matter. It is the primary center for the regulation and control of bodily activities, receiving and interpreting sensory impulses, and transmitting information to the muscles and body organs. It is also the seat of consciousness, thought, memory, and emotion.

Dementia: Significant loss of intellectual abilities such as memory capacity, severe enough to interfere with social or occupational functioning. Criteria for the diagnosis of dementia include impairment of attention, orientation, memory, judgment, language, motor and spatial skills, and function.

Disease: any deviation from or interruption of the normal structure or function of any body part, organ, or system that is manifested by a characteristic set of symptoms and signs and whose etiology, pathology, and prognosis may be known or unknown.

Caregiver: one who contributes the benefits of medical, social, economic, or environmental resources to a dependent or partially dependent individual, such as a critically ill person.

Atrial Fibrillation: incoordinate twitching of the heart muscle fibers in which the normal rhythmical contractions of the cardiac atria are replaced by the rapid irregular twitching of the muscular wall that cause the ventricles to respond irregularly.

Hypercoaguable state: the medical term for a condition in which there is an abnormally increased tendency toward blood clotting Carotid stenosis: abnormal narrowing of the carotid artery, often a preamble to a stroke Carotid artery: a key artery located in the front of the neck through which blood from the heart goes to the brain LDL cholesterol: Lipoproteins which are combinations of lipids (fats) and proteins are the form in which lipids are transported in the blood. The low-density lipoproteins transport cholesterol from the liver to the tissues of the body. LDL cholesterol is therefore considered the "bad" cholesterol.

Systolic: The blood pressure when the heart is contracting. It is specifically the maximum arterial pressure during contraction of the left ventricle of the heart. The time at which ventricular contraction occurs is called systole.

Diabetes Mellitus (DM): A chronic disease that occurs when the pancreas does not produce enough insulin, or alternatively, when the body cannot effectively use the insulin it produces. Insulin is a hormone that regulates blood sugar.

HgbA1c: A test that measures the amount of hemoglobin bound to glucose. It is a measure of how much glucose has been in the blood during the past two to four months.

Chronic inflammation: prolonged and persistent inflammation marked chiefly by new connective tissue formation; it may be a continuation of an acute form or a prolonged low-grade form.

C-reactive protein (CRP): A plasma protein that rises in the blood with the inflammation from certain conditions.

Magnetic Resonance Imaging (MRI): a noninvasive medical diagnostic technique in which the absorption and transmission of high-frequency radio waves are analyzed as they irradiate the hydrogen atoms in water molecules and other tissue components placed in a strong magnetic field. This computerized analysis provides a powerful aid to the diagnosis and treatment planning of many diseases, including cancer.

Electrocardiograph (EKG): An instrument used in the detection and diagnosis of heart abnormalities that measures electrical potentials on the body surface and generates a record of the electrical currents associated with heart muscle activity.

30 day monitor: a portable electrocardiograph worn by a client over an extended period of time to assess the effects on heart function of activities of daily living.

ASA: aspirin: A white crystalline compound derived from salicylic acid and used in medicine to relieve fever and pain and as an anticoagulant.

Neuropsychiatric Evaluation: a testing method through which a neuropsychologist can acquire data about a subject's cognitive, motor, behavioral, language, and executive functioning. In the hands of a trained neuropsychologist, these data can provide information leading to the diagnosis of a cognitive deficit or to the confirmation of a diagnosis, as well as to the localization of organic abnormalities in the central nervous system (CNS); the data can also guide effective treatment methods for the rehabilitation of impaired clients.

While the invention has been described in detail and with reference to specific embodiments thereof, it will be apparent to one skilled in the art that various changes and modifications can be made therein without departing from the spirit and scope thereof.

What is claimed is:

1. A method for the prevention of dementia, comprising:
    (a) testing, in a client, for a plurality of risk factors selected from the group consisting of brain tissue, atrial fibrillation, hypercoaguable state, LDL cholesterol, carotid artery evaluation, tobacco use, hypertension, inflammation evaluation;
    (b) determining a score for each of the risk factors tested, wherein each score is based on a continuous scale from a low number to a high number, wherein a low number corresponds to a relatively high likelihood of dementia risk and a high number corresponds to a relatively low likelihood of dementia risk;
    (c) applying all of the scores obtained to an equation that yields a resulting value proportional to an overall risk of dementia; and
    (d) providing dementia risk reduction advice to the client to lower the scores for each of the factors.

2. The method for prevention of dementia of claim 1, wherein the step of testing comprises testing all of the factors, including brain tissue, atrial fibrillation, hypercoaguable state, LDL cholesterol, carotid artery evaluation, tobacco use, hypertension, and inflammation evaluation.

3. The method of prevention of dementia of claim 1, wherein the method is performed by center specializing in medical prevention and the testing is certified for quality of consistency by the center.

4. The method of prevention of dementia of claim 1, wherein the equation is:

$$n = \frac{500}{4\pi a^2} + \frac{1000}{4\pi b^2} + \frac{1000}{4\pi g^2} + \frac{1100}{4\pi c^2} + \frac{600}{4\pi h^2} + \frac{900}{4\pi t^2} + \frac{800}{4\pi y^2} + \frac{900}{4\pi d^2} + \frac{400}{4\pi i^2} + \frac{1100}{4\pi x^2}$$

where:
  n=a value used in risk of dementia score/final score expressed as a percent of chance to develop dementia in this client;
  a=a value calculated from atrial fibrillation the factor;
  b=a value calculated from brain tissue factor;
  g=a value calculated from LDL factor;
  c=a value calculated from carotids factor;
  h=a value calculated from hypercoaguable state factor;
  t=a value calculated from tobacco factor;
  y=a value calculated from hypertension factor;
  d=a value calculated from diabetes factor;
  i=a value calculated from systemic inflammation factor; and
  x=a value calculated from secondary the factors.

* * * * *